United States Patent
Helmberger et al.

(10) Patent No.: US 7,507,080 B2
(45) Date of Patent: Mar. 24, 2009

(54) APPARATUS FOR THE MANUFACTURE OF MUFFLES FOR THE PRODUCTION OF DENTAL PROSTHETIC PARTS

(75) Inventors: Martin Helmberger, Traunstein (DE); Stephan Miller, Traunstein (DE)

(73) Assignee: DEKEMA Dental-Keramikoefen GmbH, Freilassing (DE)

( * ) Notice: Subject to any disclaimer, the term of this patent is extended or adjusted under 35 U.S.C. 154(b) by 307 days.

(21) Appl. No.: 11/357,306

(22) Filed: Feb. 17, 2006

(65) Prior Publication Data
US 2006/0188837 A1    Aug. 24, 2006

(30) Foreign Application Priority Data
Feb. 24, 2005    (DE) ............... 20 2005 003 014 U

(51) Int. Cl.
*B28B 1/00*    (2006.01)
*A61C 13/00*    (2006.01)

(52) U.S. Cl. .............. 425/175; 249/54; 425/180; 425/DIG. 11

(58) Field of Classification Search ............ 249/54, 249/163, 164, 173, 55; 425/175–180, DIG. 11; 264/16–20; 164/DIG. 4, DIG. 14
See application file for complete search history.

(56) References Cited

U.S. PATENT DOCUMENTS

| | | | | |
|---|---|---|---|---|
| 706,016 A | * | 8/1902 | Brewer et al. | 425/179 |
| 1,962,410 A | * | 6/1934 | Rodin | 425/177 |
| 1,970,261 A | | 8/1934 | Turner | |
| 2,051,427 A | * | 8/1936 | Snavely | 269/73 |
| 2,065,977 A | * | 12/1936 | Jefferies | 164/203 |
| 3,871,804 A | * | 3/1975 | Cooper | 425/175 |

(Continued)

FOREIGN PATENT DOCUMENTS

CH    270980    12/1950

(Continued)

OTHER PUBLICATIONS

Von Ralf Suckert et. al., "Inlay-und Onlaytechnik heute Gubtechnik und Fertigstellung", *Dental-Labor*, 1990, pp. 355-372, vol. 38.

(Continued)

*Primary Examiner*—Philip C Tucker
*Assistant Examiner*—Dimple N Bodawala
(74) *Attorney, Agent, or Firm*—Townsend and Townsend and Crew, LLP

(57) ABSTRACT

An apparatus for manufacturing muffles for producing dental prosthetic parts comprises a collar divided at least once in the peripheral direction to form a receiving space for an investment material in which at least one pattern for a dental prosthetic part is arranged before the filling with the investment material. At least one pattern holder simultaneously serves as a spacer for an injection plunger passage and a base part closes an open side of the collar. Holding means encompasses the collar to hold the collar together, with the collar being conical with respect to the longitudinal axis thereof at least in one section for simpler manufacture and better handling. The holding means includes at least one ring, in particular a rigid ring, which has a conical inner surface with which it is pushed onto the conical section in the collar.

21 Claims, 2 Drawing Sheets

U.S. PATENT DOCUMENTS

| | | | | |
|---|---|---|---|---|
| 4,133,371 | A | * 1/1979 | Birch et al. | 164/350 |
| 5,792,304 | A | * 8/1998 | Tamura et al. | 156/345.27 |
| 5,858,417 | A | * 1/1999 | Bosshart | 425/192 R |
| 6,180,922 | B1 | * 1/2001 | Rohner et al. | 219/390 |
| 6,186,761 | B1 | * 2/2001 | Petkow et al. | 425/178 |
| 6,206,671 | B1 | * 3/2001 | Tsuchiya et al. | 425/145 |

FOREIGN PATENT DOCUMENTS

| | | |
|---|---|---|
| DE | 539734 | 11/1931 |
| DE | 600592 | 7/1934 |
| DE | 8108695 | 12/1981 |
| DE | 8613943 | 8/1986 |
| DE | 9001743 U1 | 4/1990 |
| DE | 9213321 U1 | 5/1993 |
| DE | 19955866 A1 | 7/2000 |
| DE | 10037352 A1 | 2/2002 |
| DE | 10037681 | 2/2002 |
| DE | 10049266 A1 | 4/2002 |
| DE | 10136584 A1 | 2/2003 |
| DE | 10241857 | 4/2003 |
| DE | 20306306 A1 | 6/2003 |
| DE | 10324404 A1 * | 12/2004 |
| DE | 10325660 A1 | 1/2005 |
| EP | 0231773 A1 | 8/1987 |
| FR | 8814789 | 5/1990 |
| JP | 10037681 A * | 2/1998 |
| WO | WO 02/38075 A1 | 5/2002 |

OTHER PUBLICATIONS

Article: Kapitel 9: Präzisions-Gubtechnik für festsitzended Zahnersatz, pp. 362-400. Published on 1996.

* cited by examiner

APPARATUS FOR THE MANUFACTURE OF MUFFLES FOR THE PRODUCTION OF DENTAL PROSTHETIC PARTS

CROSS-REFERENCE TO RELATED APPLICATIONS

This application claims the benefit of German Utility Model No. DE 20 2005 003 014.7, filed on Feb. 24, 2005, the disclosure of which is incorporated herein by reference.

FIELD OF THE INVENTION

The present invention relates to an apparatus for the manufacture of muffles for the production of dental prosthetic parts.

BACKGROUND OF THE INVENTION

An apparatus of the prior art is known, for example, from the German patent DE 600 592. In this apparatus, the holding means for the holding together of the collar is formed by a screw connection with a singly divided collar. With a two-fold divided collar, that is, a collar comprising two peripheral parts, the holding means of this known apparatus is formed by circlips or a type of bayonet fastening.

SUMMARY OF THE INVENTION

It is an underlying object of the present invention to simplify an apparatus of the prior art in manufacture and in handling.

This object is satisfied in that the collar is formed conically in at least one section with respect to the longitudinal axis of the collar and in that the holding means include at least one ring, in particular a rigid ring, which has a conical inner surface with which it can be pushed onto the conical section of the collar.

The use of a rigid ring as a holding means has the advantage that an opening of the collar on the hardening of the investment material is practically precluded. The conical design of the collar and of the inner surface of the ring permits a simple fixing and releasing of the ring. This is also simple in manufacture.

Conical sections, which are arranged symmetrically to the transverse central plane, as well as two rings with a conical inner surface are preferably arranged at both sides of the transverse central plane of the collar. A uniform counter-force can be exerted onto the collar by this design.

Particularly good results can be achieved when the collar has respective sections conically converging toward its end at the base side and toward its other end. It is particularly advantageous for the collar to converge conically overall toward its two ends. It is particular favorable in manufacture when the collar, starting from a central region, has a continuous conical convergence up to its two ends.

The conical surfaces are preferably made smooth. A release of the rings from the collar is thereby simplified. By selecting an angle of inclination of smaller than 8° to the longitudinal axis of the collar, an unintentional release of the rings due to the expansion force of the investment compound can be prevented by frictional retaining despite smooth surfaces.

In particular plastic has proved advantageous as the material for the collar. Transparent plastic can also be used for the collar. This has the advantage that the position of the dental prosthesis patterns can also be inspected with a closed collar before and during the filling with the investment compound. The rings preferably consist of metal, in particular of aluminum.

For the better release of the rings, the holding means preferably have a rough or structured surfaced on their outer side. The rings can, for example, be provided with a corrugation.

In accordance with a further embodiment of the invention, which is also claimed per se, the collar consists of more than two parts which each form a peripheral section of the collar. When more than two parts are used, it is easier to check whether a positioned pattern is correctly positioned in the apparatus. It can hereby above all be more easily ensured that no pattern gets too close to the collar. For this purpose, a collar part is connected to the base part and a pattern with a holder is arranged in the designated position. It can be determined by moving the collar part around the base part and by a visual inspection whether the pattern gets too close to the collar. When only two parts are used, in contrast, a check is made more difficult since the pattern is already covered at the side by a collar part.

The use of three collar parts has proved to be advantageous. On the one hand, this is favorable in manufacture and, on the other hand, it is sufficient to permit a visual inspection. In addition, the simple assembly of the collar is thereby possible and the force distribution is optimized, in particular when all the collar parts have the same size. It is in addition particularly advantageous for manufacture for all collar parts to be made completely the same as one another.

In accordance with a further embodiment of the invention, which is also likewise claimed independently, the apparatus is part of a system which has different collars for different muffle sizes as well as common parts which can be combined selectively with the different collars. A common base part can, for example, be provided which is combined with different collar parts depending on which size the receiving space for the investment compound should have. In this manner, the size of the receiving space can be adapted to the size and/or number of the dental prosthesis patterns and the customary investment compounds amounts of 100 g, 200 g and 300 g can be used selectively.

It is particularly advantageous for all parts, except for the collars, to be made as common parts. In particular a cover part and the holding means can also be made as common parts in addition to the base part. Only different collar parts thereby have to be kept in stock to realize receiving spaces of different size.

In accordance with yet another embodiment of the invention, which is also likewise claimed independently, the collar has, in the direction of its longitudinal axis, a first section with a first internal diameter and a second section with a second internal diameter as well as a step therebetween, with the first internal diameter being larger than the second internal diameter. The volume of the receiving space can be kept small due to this stepped embodiment of the collar since a lower volume is required in the region of the pattern holders. The first section therefore preferably extends over the region in which the dental prosthetic patterns are located and the second section extends over the region in which the pattern holders are located.

On the one hand, investment material can hereby be saved and, on the other hand, a faster heat penetration of the investment compound, of the ceramic material and of the spacer for the injection plunger, that is, of the pattern holder, results. Furthermore, time can be saved in the exposure of the dental prosthesis part.

In accordance with yet another embodiment of the invention, which is also likewise claimed independently, the base part is made as a pedestal onto which a plurality of pattern carriers, in particular comprising material which can be burned out, melted out or removed in another manner, for example chemically, can be mounted, and radial ray markings are provided on the upper side of the pedestal for the positioning of the pattern carriers. The positioning of the pattern carriers is simplified thereby such that the available space can be utilized ideally. More dental prosthetic parts can thereby be produced in one workstep. The positioning is particularly simplified when, in accordance with a further embodiment of the invention, markings are additionally provided which extend transversely to the ray markings and which in particular form a cobweb-like marking.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
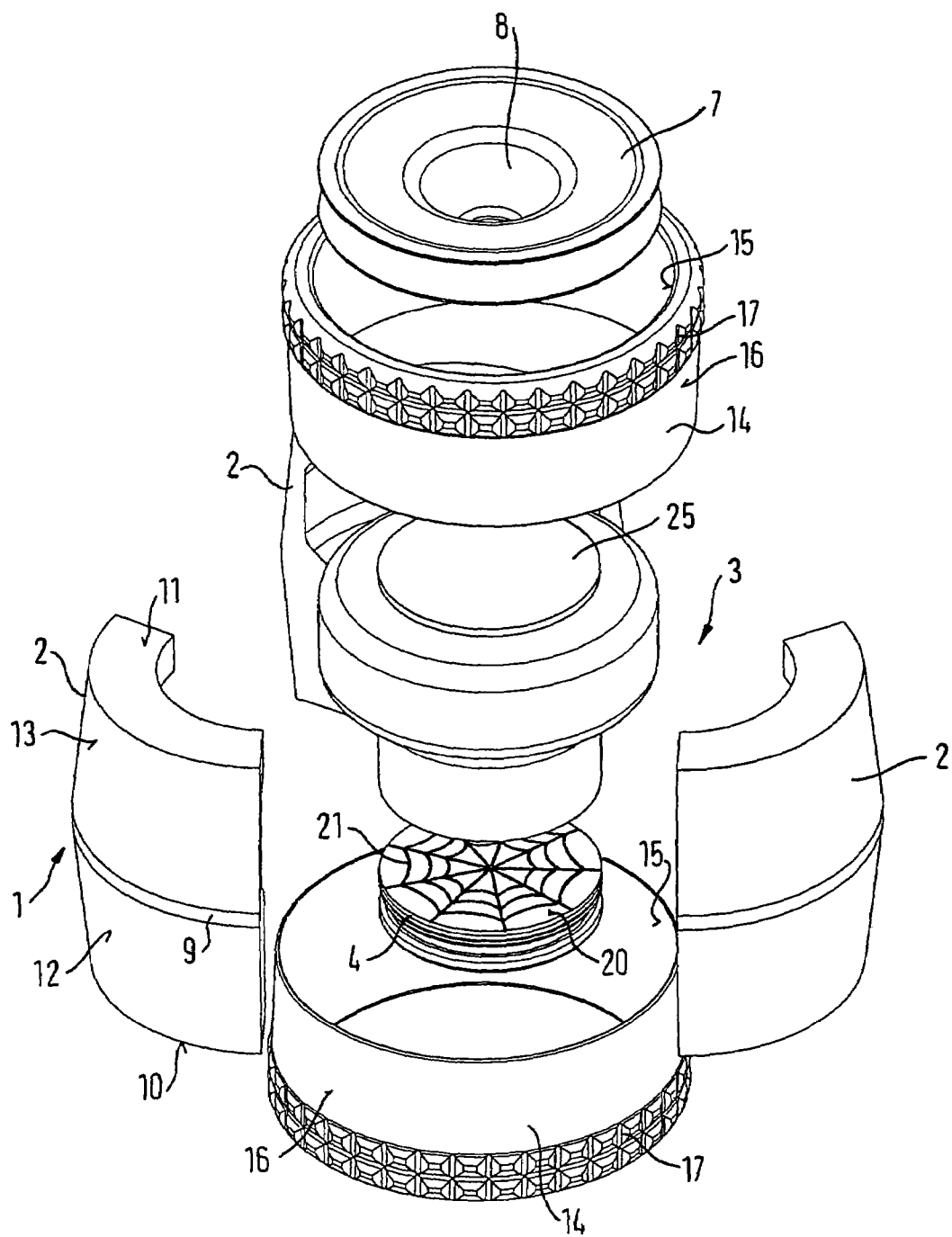
FIG. 1 illustrates a perspective exploded representation of an apparatus in accordance with the invention with muffle.

The following description of the preferred embodiment(s) is merely exemplary in nature and is in no way intended to limit the invention, its application, or uses.

The apparatus shown includes a collar 1 with three segments 2 which are each made the same as one another and which can be combined to form a collar forming a receiving space 3. The apparatus furthermore includes a pedestal 4 which can be set into the lower opening 5 of the collar 1 and terminates it. A cover part 7 with a filling funnel 8 is inserted into the upper opening 6 of the collar 1.

Figure 2:
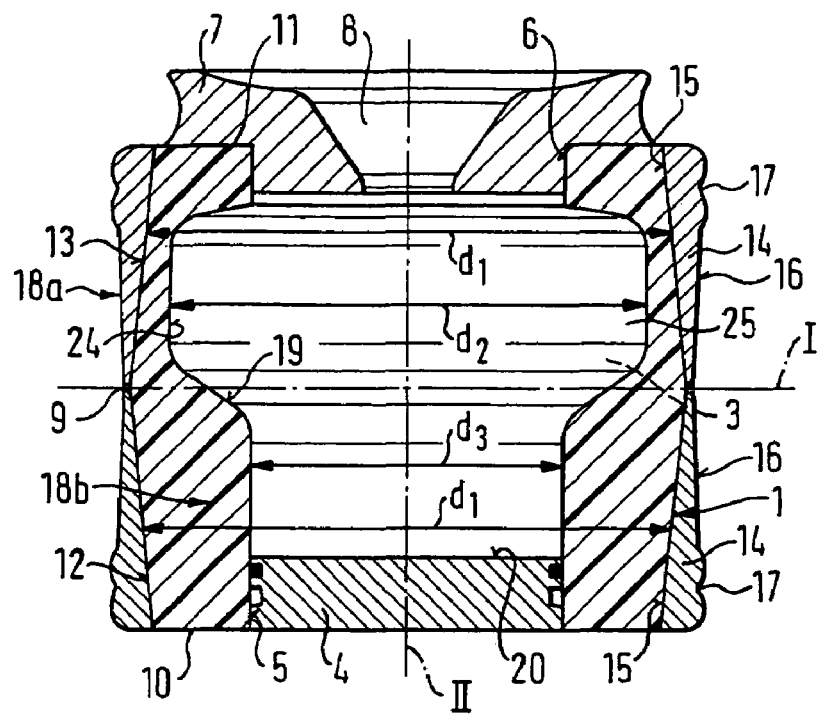
FIG. 2 illustrates a vertical section through the apparatus of FIG. 1.

As can in particular be recognized in FIG. 2, the segments 2, and thus the collar 1, converge, starting from a central region 9, in a continuous manner up to their two ends 10, 11. A holding ring 14 whose internal diameter $d_1$ converges conically accordingly can in each case be mounted on the two conical sections 12 and 13 of the collar 1 formed thereby. The conical areas 12, 13 are made in specular symmetry to the transverse central plane I of the collar 1. Accordingly, the two holding rings 14 are made the same as one another, but are mounted onto the collar 1 with opposite orientation.

The surfaces of the conical sections 12 and 13 of the collar 1 and of the inner periphery 15 of the holding rings 14 are each smooth. The rings 14 can therefore easily be rotated with respect to the collar 1. To further facilitate the rotation, the holding rings 14 are additionally provided in a part of their outer periphery 16 with a structuring 17 in the form of a notch or corrugation.

The conical surfaces 12, 13 of the collar 1 and the conical inner periphery 15 of the holding rings 14 each have an angle of inclination smaller than 8° to the longitudinal axis 11 of the collar 1. It is thereby ensured that, when a radially outwardly directed force is applied to the segments 2 of the collar 1, the holding rings 14 do not slide off the collar 1, but counteract an opening of the collar by friction retention. The holding rings 14 can, however, be released easily by rotation about the longitudinal axis 11 of the collar 1 and a subsequent pulling off upwardly or downwardly. This is simplified by the smooth surfaces. The holding rings 14 are in particular rigid and made of aluminum. The segments 2 of the collar 1 consist of plastic.

As can in turn best be recognized in FIG. 2, the segments 2, and thus the collar 1, each have a first section $18_a$ with a first internal diameter $d_2$ and a second section $18_b$ with an internal diameter $d_3$ which is smaller in comparison with the former in each case in the direction of the longitudinal axis II of the collar 1. A step 19 is provided between the first section $18_a$ and the second section $18_b$ and connects both sections to one another. The volume of the receiving space 3 is thereby larger in the upper region of the collar than in the lower region. The dental prosthesis patterns are located in the upper region, while the pattern carriers are located in the lower region and simultaneously serve as spacers for the injection plunger passages.

Figure 3:
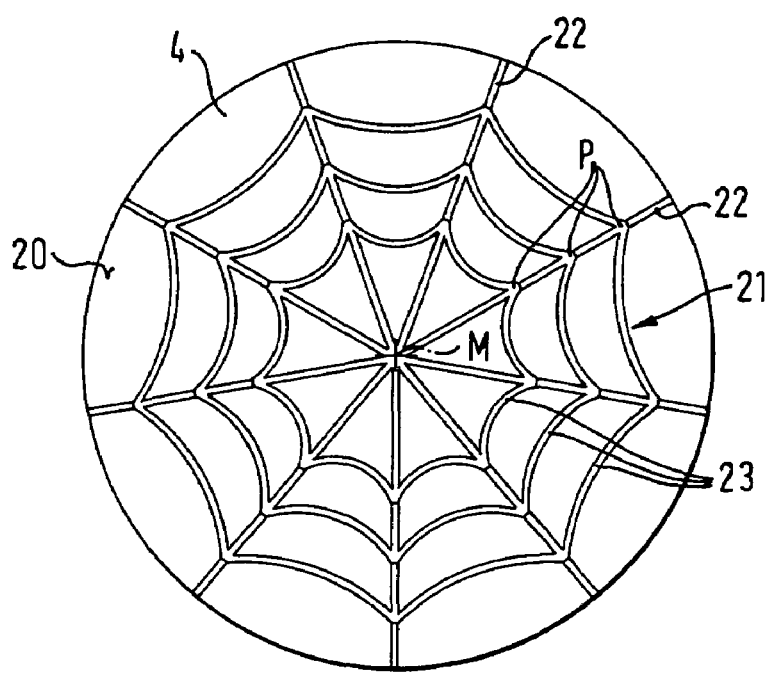
FIG. 3 illustrates a plan view of a part of the apparatus of FIG. 1.

It can in particular be recognized in FIG. 3 that a marking 21 is present on the upper side 20 of the pedestal 4 in the form of a cobweb which includes, in addition to radial ray markings 22, markings 23 extending transversely thereto. The radial ray markings 22 are arranged uniformly around the center M of the pedestal 4 and the transverse markings 23 have approximately the same radial spacing from one another. The points of intersection P of the cobweb marking 21 represent preferred positions for the pattern carriers which can be positioned on the pedestal 4.

One or more pattern carriers with patterns are placed onto the pedestal 4 to manufacture a muffle with the apparatus in accordance with the invention. Then a check can be made, by putting on a segment 2 of the collar 1, whether the patterns come too close to the inner side 24 of the collar 1. For this purpose, the one segment 2 can be moved around the pedestal 4 to check the total periphery. A visual inspection can be carried out easily due to the size of the segment amounting only to a third of the total periphery.

If no problems can be recognized in this process, the two other segments 2 of the collar 1 are added and the collar 1 is completed. Then the two holding rings 14 are pushed onto the collar 1 from above and from below. The cover 7 with the filling funnel 8 is subsequently inserted. The investment compound can now be filled through the funnel 8 into the receiving space 3 of the muffle form in accordance with the invention and hardened. The holding rings 14 prevent an opening of the collar 1 by an expansion of the investment compound during hardening.

After the hardening of the investment compound, the rings 14 are removed from the collar 1 by rotation. The segments 2, the pedestal 4 and the cover 7 are then removed. The invested patterns and the pattern holders can subsequently be burned out or melted out. The muffle 25 of investment material remains behind with the passages for the injection plunger and the hollow spaces for the reception of the dental prosthesis material in the form of the finished dental prosthesis. The dental prosthesis can then be produced in a known manner with this muffle and is then removed from the muffle by sandblasting, for example.

In addition to the segments 2 of the collar 1 shown, further segments can be provided which each likewise form a collar, with the receiving spaces 3 being different from one another, in particular having a different size. The segments 2 are made such that they can be combined with the same pedestal 4, the same cover 7 and the same retaining rings 14. A system thereby results for the manufacture of muffles of different sizes, and possibly shapes, which is cost-favorable in manufacture and storage. The handling is also thereby simplified.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An apparatus for the manufacture of muffles for the production of dental prosthetic parts comprising:
   a collar divided at least once in a peripheral direction to form a central receiving space for an investment material in which at least one pattern for a dental prosthetic part is arranged prior to a filling with the investment material and held by;
   at least one pattern holder that simultaneously serves as a spacer for an injection plunger passage; and
   a base part which closes an open side of the collar as well as a holder enveloping the collar to hold the collar together, wherein the collar is conical at least in one section with respect to a longitudinal axis (II) of the collar, and wherein the holder includes at least one ring, which has a conical inner surface with which it is pushed onto the conical section of the collar.

2. An apparatus in accordance with claim 1, wherein conical sections, which are arranged symmetrical to a transverse central plane (I), are provided at both sides of the transverse central plane (I) of the collar, and wherein two holding rings with a conical inner surface are provided.

3. An apparatus in accordance with claim 1, wherein the collar has respective sections conically converging toward its end at a base side and toward its other end.

4. An apparatus in accordance with claim 3, wherein the collar converges conically overall toward its two ends.

5. An apparatus in accordance with claim 4, wherein the collar converges conically, starting from a central region, in a continuous manner up to its two ends.

6. An apparatus in accordance with claim 1, wherein the conical surfaces are smooth.

7. An apparatus in accordance with claim 1, wherein the conical surfaces have an angle smaller than 8° with respect to the longitudinal axis (II) of the collar.

8. An apparatus in accordance with claim 1, wherein the collar consists of plastic.

9. An apparatus in accordance with claim 1, wherein the holder consists of metal, in particular of aluminum.

10. An apparatus in accordance with claim 1, wherein the holder has a rough or structured surface on their outer side.

11. An apparatus in accordance with claim 1, wherein the collar consists of more than two parts which each form a peripheral section of the collar.

12. An apparatus in accordance with claim 11, wherein the collar consists of three parts.

13. An apparatus in accordance with claim 11, wherein all of the parts have the same size.

14. An apparatus in accordance with claim 11, wherein all of the parts are made identical with respect to one another.

15. An apparatus in accordance with claim 1, comprising a plurality of interchangeable collars, each of which corresponds to a different muffle size as well as common parts that are selectively combinable with one of said plurality of collars, wherein each of said collars is divided at least once in the peripheral direction to form said receiving space.

16. An apparatus in accordance with claim 15, wherein all of the parts, except for the plurality of collars, are made as common parts, in particular the base part, a cover part and the holder.

17. An apparatus in accordance with claim 1, wherein the collar has a first section with a first internal diameter ($d_2$) and a second section with a second internal diameter ($d_3$) along its longitudinal axis (II), as well as a step therebetween, with the first internal diameter ($d_2$) being larger than the second internal diameter ($d_3$).

18. An apparatus in accordance with claim 17, wherein the first section extends over a first region configured to locate dental prosthetic patterns and the second section extending over a second region configured to locate the pattern.

19. An apparatus in accordance with claim 1, wherein the base part is made as a pedestal onto which a plurality of pattern carriers can be mounted which are in particular of a material which can be one of burned out, melted out and chemically removed, and wherein radial ray markings are provided on an upper side of the pedestal for positioning of the pattern carriers.

20. An apparatus in accordance with claim 19, wherein transverse markings extending transversely to the radial ray markings are provided to form a cobweb-like marking.

21. An apparatus for the manufacture of muffles for the production of dental prosthetic parts comprising:
   a collar divided at least once in a peripheral direction to form a substantially central receiving space for holding an investment material, wherein an outer surface of the collar is conical at least in one section with respect to a longitudinal axis (II) of the collar; and
   a holder enveloping the collar to hold the collar together, wherein the holder has conical inner surface to frictionally engage with the outer surface of the collar.

* * * * *